United States Patent [19]

Press et al.

[11] 4,219,656

[45] Aug. 26, 1980

[54] 3,4-DISUBSTITUTED THIOPHENES

[75] Inventors: Jeffery B. Press, Bellvale, N.Y.; Sidney R. Safir, River Edge, N.J.

[73] Assignee: American Cyanamid Company, Stamford, Conn.

[21] Appl. No.: 954,268

[22] Filed: Oct. 24, 1978

[51] Int. Cl.$^2$ .......................................... C07D 333/38
[52] U.S. Cl. ...................................... 549/64; 424/275
[58] Field of Search ...................... 260/332.26; 549/64

[56] References Cited

FOREIGN PATENT DOCUMENTS 2615885  10/1977  Fed. Rep. of Germany ...... 260/332 X

*Primary Examiner*—Robert Gerstl
*Attorney, Agent, or Firm*—Edward A. Conroy, Jr.

[57] ABSTRACT

This application discloses novel substituted 4-(alkoxy or alkanoyloxy)-3-thiophenecarboxylic acids, esters, and amides which possess analgesic and antipyretic activity in warm-blooded animals.

2 Claims, No Drawings

3,4-DISUBSTITUTED THIOPHENES

BRIEF SUMMARY OF THE INVENTION

This invention relates to new organic compounds and, more particularly, is concerned with novel substituted 4-(alkoxy or alkanoyloxy)-3-thiophenecarboxylic acids, esters, and amides which may be represented by the following structural formula:

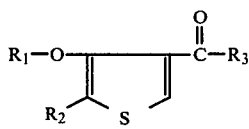

wherein $R_1$ is hydrogen, alkyl having from 2 to 3 carbon atoms or alkanoyl having from 2 to 4 carbon atoms; $R_2$ is hydrogen or chloro with the proviso that $R_1$ may not be hydrogen or alkanoyl when $R_2$ is chloro; and $R_3$ is hydroxy, alkoxy having from 1 to 3 carbon atoms, amino or anilino. The invention also includes the pharmacologically acceptable cationic salts thereof when $R_3$ is hydroxy.

DETAILED DESCRIPTION OF THE INVENTION

The useful pharmaceutically acceptable salts of the above structural formula are those with pharmacologically acceptable metal cations, ammonium, amine cations, or quaternary ammonium cations. Preferred metal cations are those derived from the alkali metals, e.g. lithium, sodium and potassium, and from the alkaline earth metals, e.g. magnesium and calcium, although cationic forms of other metals, e.g. aluminum, zinc, iron and in particular copper, are within the scope of the invention.

Pharmacologically acceptable amine cations are those derived from primary, secondary or tertiary amines such as mono-, di- or trimethylamine, ethylamine, dibutylamine, triisopropylamine, N-methylhexylamine, decylamine, dodecylamine, allylamine, crotylamine, cyclopentylamine, dicyclohexylamine, mono- or dibenzylamine, $\alpha$, or $\beta$-phenylethylamine, ethylenediamine, diethylenetriamine, and arylaliphatic amines containing up to and including 18 carbo atoms, as well as heterocyclic amines, e.g. piperidine, morpholine, pyrrolidine, piperazine and lower alkyl derivative thereof, e.g. 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g. mono-, di-, or triethanolamine, ethyldiethanolamine, N-butylethanolamine, 2-amino-1-butanol, 2-amino-2-ethyl-1,3-propanediol, 2-amino-2-methyl-1-propanol, tris(hydroxy-methyl)aminomethane, N-phenylethanolamine, N-(p-tert-amylphenyl)diethanolamine. Examples of suitable pharmacologically acceptable quaternary ammonium cations are tetramethylammonium, tetraethylammonium, benzyltrimethylammonium, phenyltrimethylammonium, and the like.

The novel compounds of the present invention may be readily prepared as set forth in the following reaction scheme:

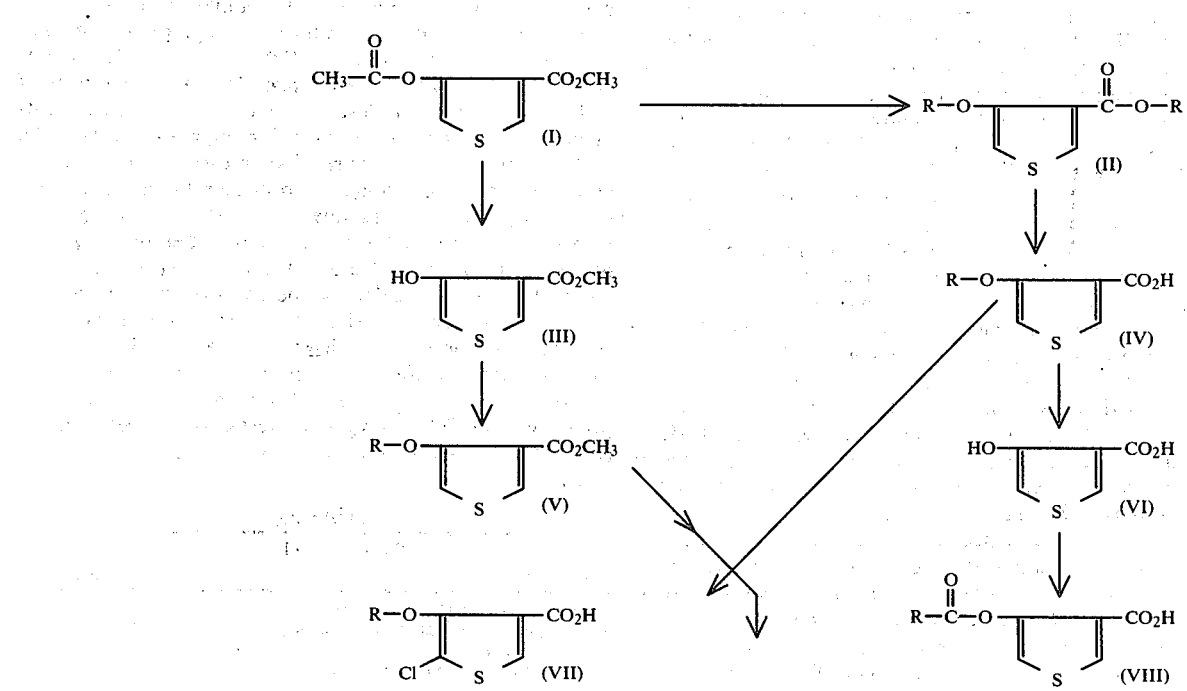

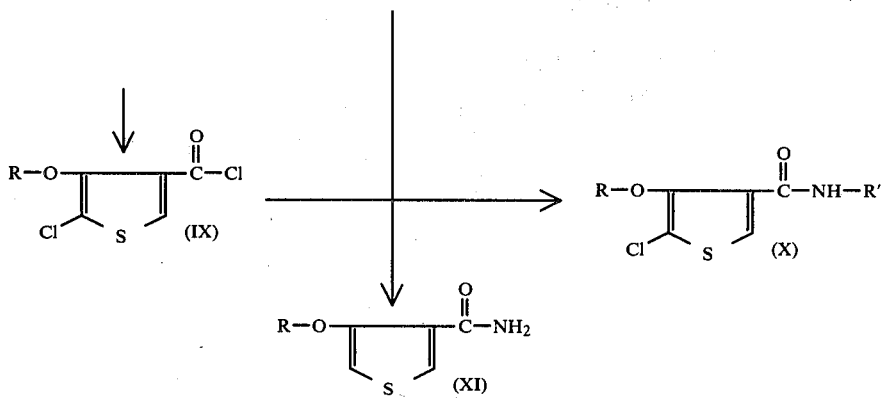

wherein R is alkyl having from 1 to 3 carbon atoms and R' is hydrogen or phenyl. In accordance with the above reaction scheme, methyl 4-acetyloxy-3-thiophenecarboxylate (I) is treated with an alkanol of the formula R—OH in the presence of conc. sulfuric acid at the reflux temperature for 3–7 days to provide the corresponding 4-alkoxy-3-thiophenecarboxylic acid, alkyl ester (II). Concentration of the reaction mixture followed by dilution with water and extraction with diethyl ether provides the product (II) upon stripping of the ether and distillation. Treatment of the methyl ester (I) with p-toluenesulfonic acid in methanol and distillation in vacuo of the residual product provides the 4-hydroxy-3-thiophenecarboxylic acid, methyl ester (III). When (III) is treated with an ethereal solution of a diazoalkane having from 1 to 3 carbon atoms for 2–7 days at room temperature, 4-alkoxy-3-thiophenecarboxylic acid, methyl ester (V) is produced. When the alkyl ester (II) is refluxed for 1–6 hours with ethanolic potassium hydroxide, acidified with 5 N sulfuric acid, extracted with methylene chloride and precipitated with petroleum ether, the 4-alkoxy-3-thiophenecarboxylic acid (IV) is produced. Treatment of (IV) with boron tribromide in methylene chloride for 16–40 hours and extraction with diethyl ether provides the 4-hydroxy-3-thiophenecarboxylic acid compound (VI). When (VI) is treated with an alkanoic anhydride of the formula (RCO)₂O and concentrated sulfuric acid and the product is extracted from aqueous solution with methylene chloride, 4-alkanoyloxy-3-thiophenecarboxylic acid (VIII) is obtained. When (IV) is treated with sulfuryl chloride in chloroform at room temperature, 5-chloro-4-alkoxy-3-thiophenecarboxylic acid (VII) is produced. The addition of thionyl chloride to the acids (IV, VI, VII or VIII) with warming at 80°–120° C. for 1–3 hours and distillation of the residue in vacuo provides the corresponding substituted 3-thiophenecarbonyl chlorides (such as IX). Treatment of the acid chlorides with ice-cold concentrated ammonium hydroxide or aniline in methylene chloride yields the corresponding substituted 3-thiophenecarboxamides (such as X). Like wise, treatment of the esters (I, II, III or V) with ammonium hydroxide for 2–7 days at room temperature provides the corresponding substituted 3-thiophenecarboxamides (such as XI).

The novel compounds of the present invention are physiologically active on the central nervous system and possess activity as analgetic agents as well as antipyretic agents. Representative compounds of the present invention exhibit analgesic activity when measured by a modification of the method of D. C. Atkinson and A. Cowan, J. Pharm. pharmacol. 26, 727 (1974). In this test male, albino Wistar strain rats from Royalhart farms, weighing 120–150 g. are deprived of food for about 20 hours. A 40% suspension of brewers' yeast in physiological saline is injected, at a concentration of 0.25 ml./rat into the plantar surface of the left hind paw of each rat. Three hours later at which time an inflammation of the injected paw has developed, a pre-drug assessment of walking gait is made for each rat according to the following scoring system:

0 = Normal gait in the presence of a severely inflammed paw. There is continuous use of the foot pad.

0.5 = As above with intermittent mild limping.

1.0 = Constant limping, but continuous use of the foot pad.

1.5 = Limping with occasional three-legged gait (paw kept off walking surface) or intermittent use of digits in combination with foot pad.

2.0 = Continuous three-legged gait and/or only the tips of the digits touch the walking surface. There is no use of the foot pad.

More than 95% of the rats exhibit a gait score of 2 before given a test compound. Compounds, in a suitable vehicle, are administered orally by gavage or subcutaneously in a volume of 0.5 ml./100 g. of body weight. One and/or two hours later a post-drug assessment of walking gait is made as described above. The post-treatment score is then measured and compared with the pretreatment score. These results are used for determination of screening activity, for dose response estimates of potency, etc. For example, when screening experiments are carried out using 3 animals per dose, the pretreatment score is 6(2.0×3) and a post-treatment score of 4 (for 3 animals) may be considered as significant activity over parallel controls. For dose-response estimates, an individual animal may be considered to show an analgesic effect when there is a ≥50% reversal of the abnormal gait score (≤1.0 post-drug) from the pre-drug score (2.0). Compounds tested and found to be active by the above procedure are listed in Table I below.

Table I

| Walking Gait Test | |
|---|---|
| Compound | Result |
| 4-Ethoxy-3-thiophenecarboxamide | Active |
| 4-Hydroxy-3-thiophenecarboxylic acid, methyl ester | Active |
| N-(4-Ethoxy-3-thienyl)acetamide | Active |

Table I-continued

| Walking Gait Test | |
|---|---|
| Compound | Result |
| N-(4-Ethoxy-3-thienyl)formamide | Active |
| 4-Hydroxy-3-thiophenecarboxylic acid, acetate | Active |
| 5-Chloro-4-ethoxy-3-thiophenecarboxamide | Active |

The effect of compounds on experimental elevated temperature is examined during the analgesic gait test. The body temperature of rats increases after the plantar injection of brewer's yeast and thus provides a good experimental model for studying antipyresis. Rectal temperature of each rat is measured immediately after scoring the abnormal gait, by the means of a Yellow Springs Tele-Thermometer equipped with a rectal probe. The rats are then treated with the compounds at a safe screening dose and the post-treatment temperature is measured 90 minutes later. An average change of each group of rats is calculated from the difference of pre- and post-drug administration temperatures. The test has two stages:

STAGE I (3 RATS)

(A) A compound is considered active if the average temperature falls 1.6° F. or more.

(B) The test is repeated if the average temperature increases less than 0.1° F., or if the temperature falls.

STAGE II (6 RATS)

After the second experiment an average temperature of 6 rats is calculated. A compound is accepted as a potential antipyretic if the average temperature falls 0.2° F. or more. The second stage experiment depends on the result of the analgesic gait test; only compounds which are active in the gait test are tested in the second stage antipyresis. Compounds of the present invention tested for antipyresis and results thereof are listed in Table II below.

Table II

| Antipyretic Action | |
|---|---|
| Compound | Result |
| 4-Ethoxy-3-thiophenecarboxamide | Active |
| 4-Hydroxy-3-thiophenecarboxylic acid, methyl ester | Active |
| N-(4-Ethoxy-3-thienyl)formamide | Active |
| N-(4-Ethoxy-3-thienyl)acetamide | Active |
| 4-Hydroxy-3-thiophenecarboxylic acid acetate | Active |

The anti-anxiety properties of the compounds of the present invention have been established in a test which indicates anxiolytic activity by the measure of protection from convulsions resulting from the administration of pentylenetetrazole. Graded dose levels of the test compound were administered orally, in a 2% starch vehicle, to groups of at least 5 rats. At the estimated time of peak effect, the rats were treated intravenously with pentylenetetrazole at a dose of 21 to 23 mg./kg. of body weight. This dose is estimated to cause clonic seizures in 99% of unprotected rats. The effective dose ($ED_{50}$) of the test compound for protection of 50% of the animals is calculated by the method of D. H. Finney in "Statistical Methods in Biological Assay", Second Edition, Hafner Publishing Co., New York, 1964, pp. 456–457. In a representative operation, 5-chloro-4-ethoxy-3-thiophenecarboxamide was active in this test. It has been reported [R. T. Hill and D. H. Tedeschi, "Animal Testing and Screening Procedures in Evaluating Psychotropic Drugs" in An Introduction of Psychopharmacology, Eds. R. R. Rech and K. E. Moore, Raven Press. New York, pp. 237–288 (1971)] that there is a high degree of correlation between antagonism of pentylenetetrazole seizures in rats and anti-anxiety effects in higher warm-blooded animals.

Another test which has been used to assess anti-anxiety effects is a non-conditioned passive avoidance procedure described by J. R. Vogel, B. Beer and D. E. Clody, "A Simple and Reliable Conflict Procedure for Testing Anti-Anxiety Agents", Psychopharmacologia, Vol. 21, pp. 1–7 (1971). A conflict situation is induced in rats by a modification of this method. To groups of six naive Sprague-Dawley rats (200–220 grams), previously deprived of water for forty-eight hours and food for 24 hours are administered graded oral doses of test compound suspended in 2% starch vehicle also containing 2 drops of polyethylene glycol and polysorbate 80, or vehicle alone (controls). At the time of peak effect each rat is placed in a plexiglass box fitted with a drinkometer circuit connected between the stainless steel grid floor and a stainless steel drinking tube inserted in a hole in one of the walls of the box. A stimulator supplying monophasic 60 cycle square wave pulses of 0.2 milliamperes peak intensity, a timer which allows alternate 5 second "shock free" and 5 second "shock available" periods during a 5 minute test period, an electromagnetic counter to count the number of shocks received by the rat during the shock available period and a delay of one half second between the successive shocks are incorporated into the drinkometer circuit. After the rat is placed in the box, it is allowed to explore and drink 10% dextrose solution supplied through the tap. After twenty seconds of continuous unpunished drinking, the timer and drinkometer circuits are activated and 5 second shock free and 5 second shock available periods alternate. The number of shocks received by the rat during a 5 minute test period is recorded. The percentage of rats that receive 9 or more shocks in 4 to 5 minutes at each dose level is used as positive response in calculation of the median effective dose ($ED_{50}$). In a representative operation, 5-chloro-4-ethoxy-3-thiophenecarboxanilide was active in this test.

The active compounds of the present invention have thus been found to be highly useful for meliorating pain in mammals when administered in amounts ranging from about 0.03 milligram to about 10.0 mg. per kilogram of body weight per day. A preferred dosage regimen for optimum results would be from about 0.1 mg. to about 5.0 mg. per kilogram of body weight per day, and such dosage units are employed that a total of from about 7.0 milligram to about 0.35 gram of active compound for a subject of about 70 kg. of body weight are administered in a 24 hour period. The dosage regimen may be adjusted to provide the optimum therapeutic response. For example, several divided doses may be administered daily or the dose may be proportionally reduced as indicated by the exigencies of the therapeutic situation. A decided practical advantage of this invention is that the active compounds may be administered in any convenient manner such as by the oral, intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols, which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to 9.0% of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg./ml. of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 0.1 and 5.0 milligrams of active compound.

The tablets, troches, pills, capsules and the like may also contain the following: a binder such as gum tragacanth, acacia, corn starch or gelatin; excipients such as dicalcium phosphate, a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

A preferred embodiment of the present invention consists of those novel compounds which may be represented by the following structural formula:

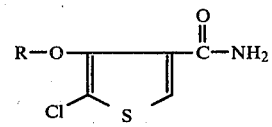

wherein R is alkyl having from 2 to 3 carbon atoms.

The invention will be described in greater detail in conjunction with the following specific examples.

EXAMPLE 1

4-Ethoxy-3-thiophenecarboxamide

A mixture of 160 g. of methyl tetrahydro-4-oxo-3-thiophenecarboxylate [R. B. Woodward et al, J. Am. Chem. Soc., 68,2232 (1946); O. Hromatka et al, Monatsh. Chem., 104, 1520 (1973)] and 1.0 g. of p-toluenesulfonic acid is refluxed overnight in isopropenyl acetate. Excess solvent is removed through a Vigreux column and the residue is distilled in vacuo bp. 94°–96° C. to give 179.5 g. of 2,5-dihydro-4-hydroxy-3-thiophenecarboxylic acid, methyl ester, acetate as a solid.

The product above (179.5 g.) in 375 ml. of methylene chloride is cooled to −25° C. and treated with 80 ml. of sulfuryl chloride which is added dropwise over a period of one hour to maintain −25° C. The mixture is stirred an additional 0.5 hour at −25° C., then is allowed to stir at room temperature overnight. Excess reagent and solvent are removed throught a Vigreux column and the residue is distilled in vacuo bp. 104°–106° C. to yield 158.2 g. of 4-hydroxy-3-thiophenecarboxylic acid, methyl ester, acetate, as a clear white solid.

A 50.0 g. portion of the preceding product and 4.0 ml. of concentrated sulfuric acid in 750 ml. of ethanol is refluxed for 72 hours. The mixture is concentrated to a volume of 200 ml. and diluted with 200 ml. of water. The aqueous solution is extracted with five 200 ml. portions of ether. The combined organic layer is washed with three 250 ml. portions of 1 N sodium hydroxide, then is dried with brine and anhydrous sodium sulfate. Concentration and distillation in vacuo bp. 92°–98° C. yields 38.9 g. of 4-ethoxy-3-thiophenecarboxylic acid, ethyl ester as a pale yellow liquid.

A 15.0 g. portion of the above product is treated by stirring with 150 ml. of concentrated ammonium hydroxide in a tightly sealed flask for 72 hours to give a crystalline precipitate. The precipitate is collected and dried in vacuo to yield 11.60 g. of white product. Recrystallization from methylene chloride-hexanes provides the product of the Example mp. 170.5°–171.5° C.

EXAMPLE 2

4-Hydroxy-3-thiophenecarboxylic acid, methyl ester

A mixture of 100 g. of 4-hydroxy-3-thiophenecarboxylic acid, methyl ester, acetate (prepared in Example 1) and 1.0 g. of p-toluenesulfonic acid in 300 ml. of methanol is stirred overnight. Excess reagent and solvent is removed through a Vigreux column. The residue is distilled in vacuo bp. 79° C. to provide 71.32 g. of the product of the Example as a clear white solid mp. 48.5°–49.5° C.

EXAMPLE 3

4-Hydroxy-3-thiophenecarboxylic acid acetate

A 20.0 g. portion of 4-ethoxy-3-thiophenecarboxylic acid, ethyl ester (prepared in Example 1) is treated with a solution of 10.0 g. of potassium hydroxide in 225 ml. of ethanol:water (8:1) and refluxed for 2 hours. The mixture is cooled, concentrated to a volume of 50 ml. and acidified with 5 N sulfuric acid. The product is extracted with five 50 ml. portions of methylene chloride. The combined organic extract is treated with activated charcoal, dried over anhydrous sodium sulfate and concentrated to a volume of 100 ml. The concentrate is treated with 100 ml. of petroleum ether and several crops of white crystalline product are collected and combined to yield 16.16 g. of 4-ethoxy-3-thiophenecarboxylic acid.

A 10.3 g. portion of the above product in 500 ml. of methylene chloride is added to 30.0 g. of boron tribromide in methylene chloride and allowed to stand overnight. The reaction mixture is treated with 250 ml. of water, stirred 0.5 hour and extracted with three 250 ml. portions of ether. The combined organic layer is treated with activated charcoal, dried over sodium sulfate and evaporated to provide 8.24 g. of 4-hydroxy-3-thiophenecarboxylic acid as a yellow crystalline solid.

A 5.03 g. portion of the preceding product (prepared as described above) is treated with 15 ml. of acetic anhydride and 1 drop of concentrated sulfuric acid with stirring. The reaction mixture is poured into 150 ml. of water and warmed on a steam bath to decompose the excess anhydride. The aqueous layer is extracted with three 50 ml. portions of methylene chloride. The combined organic layer is washed with water, treated with activated charcoal, dried over anhydrous sodium sulfate and evaporated to give a yellow gummy solid. The material is recrystallized from ethyl acetate-petroleum ether to yield 2.44 g. of the product of the example as a yellow crystalline solid.

EXAMPLE 4

5-Chloro-4-ethoxy-3-thiophenecarboxamide

A 5.15 g. portion of 4-ethoxy-3-thiophenecarxylic acid (prepared in Example 3) is dissolved in 10 ml. of chloroform and treated with 2.7 ml. of sulfuryl chloride. After the reaction subsides, the mixture is allowed to stand at room temperature, then is filtered to yield 5.02 g. of 5-chloro-4-ethoxy-3-thiophenecarboxylic acid as a white crystalline solid.

A 6.0 ml. portion of thionylchloride is added dropwise to the above product (5.02 g.), at room temperature. The reaction mixture is warmed at 100° C. for 2 hours, the thionyl chloride is removed in vacuo and the product is distilled in vacuo bp. 95°–97° C. to yield 4.95 g. of 5-chloro-4-ethoxy-3-thiophenecarbonyl chloride as a pale yellow liquid.

The entire product above (4.95 g.) is treated with 25 ml. of ice-cold concentrated ammonium hydroxide and the mixture is warmed to room temperature. The precipitate is collected by filtration and dried in vacuo at 80° C. to yield 4.44 g. of product. The material is recrystallized from methylene chloride-petroleum ether to provide the product of the example, mp. 139°–139.5° C.

EXAMPLE 5

Preparation of 50 mg. Tablets

| Per Tablet | | Per 10,000 Tablets |
|---|---|---|
| 0.050 gm. | 4-hydroxy-3-thiophenecarboxylic acid | 500 gm. |
| 0.080 gm. | Lactose | 800 gm. |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | Magnesium Stearate (1%) | 15 gm. |
| 0.150 gm. | | 1490 gm. |

The 4-hydroxy-3-thiophenecarboxylic acid, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 6

Preparation of Oral Suspension

| Ingredient | Amount |
|---|---|
| methyl 4-hydroxy-3-thiophenecarboxylate | 500 mg. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |
| Distilled water qs to | 100 ml. |

The sorbitol solution is added to 40 ml. of distilled water and the methyl 4-hydroxy-3-thiophenecarboxylate is suspended therein. The saccharin, sodium benzoate, flavor and dye are added and dissolved. The volume is adjusted to 100 ml. with distilled water. Each ml. of syrup contains 5 mg. methyl 4-hydroxy-3-thiophenecarboxylate.

EXAMPLE 7

Preparation of Parenteral Solution

In a solution of 700 ml. of propylene glycol and 200 ml. of water for injection is suspended 20.0 grams of sodium 4-acetyloxy-3-thiophenecarboxylate with stirring. After suspension is complete, the pH is adjusted to 5.5 with hydrochloric acid and the folume is made up to 1000 ml. with water for injection. The formulation is sterilized, filled into 5.0 ml. ampoules each containing 2.0 ml. (representing 40 mg. of drug) and sealed under nitrogen.

EXAMPLE 8

5-Chloro-4-ethoxy-3-thiophenecarboxanilide

A 4.50 g. portion of 5-chloro-4-ethoxy-3-thiophenecarbonyl chloride (prepared as in Example 4) was dissolved in 40 ml. of methylene chloride and stirred overnight with 2.8 ml. of triethylamine and 1.86 g. of aniline. The mixture was filtered and the filtrate extracted with 3 N hydrochloric acid. The methylene chloride layer was treated with activated charcoal, dried over anhydrous sodium sulfate and diluted with petroleum ether to give 3.62 g. of the product of the example as a white crystalline solid, m.p. 69° C.

EXAMPLE 9

Ethyl 4-ethoxy-3-thiophenecarboxylate

A mixture of 160 g. of methyl tetrahydro-4-oxo-3-thiophenecarboxylate [R. B. Woodward et al, J. Am. Chem. Soc., 68,2232 (1946); O. Hromatka et al, Monatsh. Chem., 104, 1520 (1973)] and 1.0 g. of p-toluenesulfonic acid is refluxed overnight in isopropenyl acetate. Excess solvent is removed through a Vigreux column and the residue is distilled in vacuo bp. 94°-96° C. to give 179.5 g. of 2,5-dihydro-4-hydroxy-3-thiophenecarboxylic acid, methyl ester, acetate as a solid.

The product above (179.5 g.) in 375 ml. of methylene chloride is cooled to −25° C. and treated with 80 ml. of sulfuryl chloride which is added dropwise over a period of one hour to maintain −25° C. The mixture is stirred an additional 0.5 hour at −25° C., then is allowed to stir at room temperature overnight. Excess reagent and solvent are removed throught a Vigreux column and the residue is distilled in vacuo bp. 104°-106° C. to yield 158.2 g. of 4-hydroxy-3-thiophenecarboxylic acid, methyl ester, acetate, as a clear white solid.

A 50.0 g. portion of the preceding product and 4.0 ml. of concentrated sulfuric acid in 750 ml. of ethanol is refluxed for 72 hours. The mixture is concentrated to a volume of 200 ml. and diluted with 200 ml. of water. The aqueous solution is extracted with five 200 ml. portions of ether. The combined organic layer is washed with three 250 ml. portions of 1 N sodium hydroxide, then is dried with brine and anhydrous sodium sulfate. Concentration and distillation in vacuo bp. 92°-98° C. yields 38.9 g. of 4-ethoxy-3-thiophenecarboxylic acid, ethyl ester as a pale yellow liquid.

EXAMPLE 10

N-(4-Ethoxy-3-thienyl)-acetamide

An 8.0 g. portion of 4-ethoxy-3-thiophenecarboxylic acid, ethyl ester (prepared in Example 9) and 5.0 ml. of hydrazine hydrate in 25 ml. of ethanol is refluxed overnight. The reaction mixture is quenched with 50 ml. of water, then is extracted with five 100 ml. portions of methylene chloride. The combined organic extracts are dried over anhydrous sodium sulfate and evaporated to yield 7.20 g. of 4-ethoxy-3-thiophenecarboxylic acid hydrazide as a white solid.

A 7.42 g. amount of the preceding product (prepared as described above) is dissolved in 100 ml. of 3 N hydrochloric acid and 150 ml. of glacial acetic acid, 150 ml. of chloroform is added and the mixture is cooled to 5° C. then a solution of 2.79 g. of sodium nitrite in 25 ml. of water is added dropwise with stirring while maintaining the reaction temperature below 8° C. After warming to ambient temperature the organic layer is separated, washed with aqueous sodium bicarbonate, dried over sodium sulfate and evaporated without heat to yield 7.27 g. of 4-ethoxy-3-thiophenecarbonyl azide as a yellow solid which is stored at 5° C.

A 1.97 g. portion of the above product in 20 ml. of acetic anhydride is refluxed for 3 hours and cooled to 5° C. Then 200 ml. of water is added and the mixture is warmed on a steam bath to decompose excess reagent. After cooling, the mixture is extracted with three 100 ml. portions of methylene chloride. The combined organic extracts are washed with aqueous sodium bicarbonate, treated with activated charcoal, dried over anhydrous sodium sulfate and evaporated to provide a brown solid. The solid is recrystallized from hexanes to yield 1.00 g. of the product of the example as a pale yellow crystalline solid, mp. 104° C.

EXAMPLE 11

N-(4-Ethoxy-3-thienyl)-formamide

A 1.97 g. portion of 4-ethoxy-3-thiophenecarbonyl azide (prepared in Example 10) is added portionwise to 5.0 ml. of 97% formic acid and heated to boiling. Excess solvent is removed through a short-path still head and the residue is distilled in vacuo, bp. 117° C. to yield 1.40 g. of crude product. The material is recrystallized from hexanes to give the purified product of the example, m.p. 112°-113° C.

We claim:
1. 5-Chloro-4-ethoxy-3-thiophenecarboxamide.
2. 5-Chloro-4-ethoxy-3-thiophenecarboxanilide.

* * * * *